United States Patent [19]

Ayes et al.

[11] 4,334,901

[45] Jun. 15, 1982

[54] RESPIRATOR CARTRIDGE

[75] Inventors: Adolfo V. Ayes, Hartford, Conn.; John A. Jones, Wilbraham, Mass.

[73] Assignee: American Optical Corporation, Southbridge, Mass.

[21] Appl. No.: 65,656

[22] Filed: Aug. 10, 1979

[51] Int. Cl.[3] .................... B01D 50/00; A61M 15/08; B01D 39/02

[52] U.S. Cl. ........................................ 55/487; 55/514; 55/527; 55/528; 55/DIG. 35; 128/206.17; 428/35

[58] Field of Search .................... 128/206.17; 55/486, 55/487, 488, 527, 528, 514, DIG. 35; 428/35

[56] References Cited

U.S. PATENT DOCUMENTS

| | | | |
|---|---|---|---|
| 3,316,904 | 5/1967 | Wall et al. | 55/DIG. 35 |
| 4,141,703 | 2/1979 | Mulchi | 55/487 |
| 4,179,274 | 12/1979 | Moon | 55/DIG. 35 |

*Primary Examiner*—William R. Dixon, Jr.
*Attorney, Agent, or Firm*—Alan H. Spencer

[57] ABSTRACT

Lower inhalation resistance in respirator cartridges designed for protection against aerosols is accomplished with lower production cost and improved design distributing aerosol loading over greater surface area of filter material.

8 Claims, 2 Drawing Figures

RESPIRATOR CARTRIDGE

BACKGROUND OF THE INVENTION

1. Field of the Invention

This invention relates to respirators with particular reference to air-filtering cartridges for protection against aerosols.

2. Discussion of the Prior Art

Prior art respirator cartridges designed for protection against aerosols such as lead fumes notably rapidly load with the aerosol materials and correspondingly increase their resistance to inhalation, i.e. airflow. Furthermore, in order to meet current industrial standards for initial and final airflow resistance and penetration of aerosol contaminants with the heretofor cartridge design parameters, the cost of materials and their assembly has become excessive particularly with the reflection of short service life due to rapid aerosol loading.

It is, accordingly, a principal object of this invention to lower the production cost of air-filtering respirator cartridges which are designed for protection against aerosols and to improve the operational efficiency of such devices.

Another object is to accomplish the foregoing by providing for distribution of aerosol loading over greater surface area of cartridge filter material with less than the usual number and size of cartridge components; and still another object is to accomplish a reduction in respirator cartridge production cost by simplification of assembly procedure.

Other objects and advantages of the invention will become apparent from the following description.

SUMMARY OF THE INVENTION

The foregoing objects and corollaries thereof are accomplished by provision of a respirator cartridge which is designed to eliminate the traditional screen between the perforated cartridge bottom and its adjacent filter component, substitute fiberglass for one of the usual two wool-felt components and minimize filter component-to-shell cementing operations along with reshaping of the initial aerosol contacting filter component for effecting greater than usual distribution of aerosol loading and lower inhalation resistance.

These and other details of the invention will become more readily apparent from the following description when taken in conjunction with the accompanying drawings.

IN THE DRAWINGS

DESCRIPTION OF THE PREFERRED EMBODIMENTS

Figure 1:
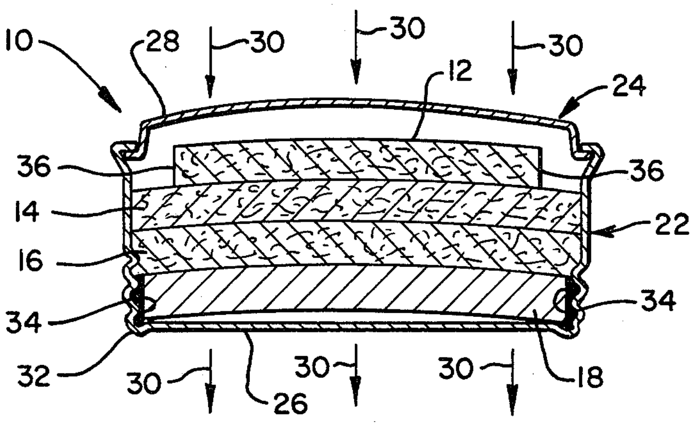
FIG. 1 is an illustration in cross-section of a preferred embodiment of the invention.
Figure 2:
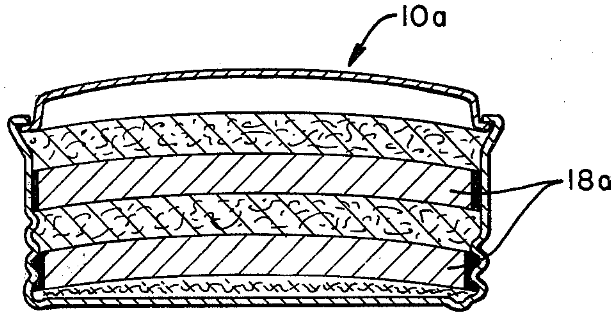
FIG. 2 (PRIOR ART)
FIG. 2 is a cross-sectional view of a typical prior art aerosol filter cartridge.

In the drawings, the structural distinctiveness of the present invention over the prior art is illustrated with FIGS. 1 and 2 wherewith the present respirator cartridge 10 (FIG. 1), when compared with prior art cartridge 10*a* (FIG. 2), can be seen to embody less components and an unusual prefilter design.

With respect to the former, the present arrangement and design of prefilter components 12, 14 16 and final filter 18 permits elimination of the prior art fine mesh screen 20 (FIG. 2) and substitution of less expensive and lighter weight glass fiber material for one of the heretofor dual wool-felt filters 18*a* (FIG. 2).

In connection with the present prefilter design, its domed triple component array provides for greater than usual distribution of aerosol loading and a correspondingly lower resistance to inhalation, i.e. airflow.

Details of the present cartridge construction are as follows:

Cartridge 10 (FIG. 1) comprises the usual shell 22 of stamped, drawn or otherwise formed sheet metal, e.g. aluminum, with cover 24 crimped in place after the positioning of filters 14, 16 and 18 in shell 22. Bottom 26 of shell 22 and top 28 of cover 24 are perforated to permit inhalation of air in the direction of arrows 30 through cartridge 10. The threaded portion 32 of shell 22 is used to conventionally secure cartridge 10 in a respirator face mask (not shown) so that top 28 of cover 24 is exposed to the particular environment against which respiratory protection is sought, e.g. an aerosol. Perforated bottom 26 of shell 22 is, accordingly, disposed internally of the respirator facepiece to provide the user with a source of filtered air for breathing.

It is to be understood that shell 22 and cover 24 may be formed of plastic or other compositions of materials which may be cast, molded or pressed to final shape.

Referring more particularly to the construction and arrangement of filters 12, 14, 16 and 18, final filter 18 of wool/acrylic felt is preferably secured in place with cement 34 while the relatively low density (e.g. non woven glass fiber) prefilter assembly of components 12, 14 and 16 is pressed into shell 22 tightly against the shell inner wall. Filter components 14 and 16 are formed to a somewhat larger diametral size than the internal diameter of shell 22 and become partially radially compressed when urged into shell 22 against final filter 18. Cement may also be used but is deemed unnecessary since the forces of inhalation which are in the direction of arrows 30 prevent displacement.

Filter 12 which is preferably cemented, stapled or otherwise attached to filter 14 domes the prefilter assembly with its edge 36 as well as face 38 exposed to incoming atmospheres, e.g. air containing an aerosol, for greater than usual surface distribution of aerosol loading.

Tests of performance of the present respirator cartridge (FIG. 1) and that of the prior art (FIG. 2) were conducted as follows with test times and conditions being identical for both structures:

Testing Atmosphere

Lead fume aerosol at a concentration of from 15 to 20 milligrams/cubic meter.

Temperature

78°-83° F.

Relative Humidity 30 to 40%

Test Flow Rate 16 liters/minute

Results (1) The present cartridge construction (FIG. 1) showed an initial resistance to airflow of from 12 to 13 mm $H_2O$ and a final resistance to airflow of from 35 to 44 mm $H_2O$.

(2) The prior art construction (FIG. 2) showed an initial resistance to airflow of from 16 to 17.5 mm $H_2O$ and a final resistance of from 47 to 66 mm $H_2O$.

Neither the prior art construction (FIG. 2) nor that of the present invention (FIG. 1) exceeded a current standard for lead penetration which is set to be less than 1.5 Mg. Both cartridges remained considerably below this 1.5 Mg maximum.

From the foregoing, it can be seen that with greater than usual economy and simplification of aerosol respirator cartridge construction, the present invention contributes lowering of initial and final inhalation (airflow) resistance with high operating efficiency.

Various modifications and adaptations of the precise form of the invention described hereinabove may be made to suit particular requirements. For example, filters 12, 14 and 16 may be formed of a single unit of resin bonded non-woven glass fibers. Accordingly, it is intended that all modifications which incorporate the novel concept disclosed are to be construed as coming within the scope of the claims or the range of equivalency to which they are entitled in view of the prior art.

We claim:

1. A respirator cartridge for protection against aerosols comprising:

a main supporting shell having an inner wall of given diameter and spaced perforated bottom and cover portions;

a succession of filter components within said shell between said bottom and cover portions, at least one of which affords final filtering of air containing an aerosol passing through said shell, said one final filtering component being of substantially the same diametral dimension as said inner wall of said shell and disposed adjacent said perforations in one of said cover and bottom portions, remaining filter components constituting prefilters of which one is of appreciably smaller diametral dimension than said given diameter of said shell and disposed centrally within said shell adjacent perforations in the other of said cover and bottom portions, said one prefilter component thereby doming said succession of filter components with its edge and surrounding surface portions of the next of said succession of components immediately exposed to said aerosol containing air entering said shell through said perforations for the purpose of providing increased area of distribution of cartridge aerosol loading without increasing cartridge shell diameter whereby resistance to inhalation (airflow) is enhanced.

2. A respirator cartridge according to claim 1 wherein said one final filter component is disposed adjacent said bottom portion of said shell and said one doming prefilter component is disposed adjacent said shell cover portion, said doming prefilter component being of smaller diametral size than remainders of all of said prefilter components for effecting said exposure of respective edges thereof to said aerosol containing air entering said shell.

3. A respirator cartridge according to claim 2 wherein said one doming prefilter component is attached to an adjacent one of said remaining prefilter components.

4. A respirator cartridge according to claim 2 wherein said final filter component is formed of wool/acrylic felt and said prefilter components are formed of relatively low density non-woven glass fibers.

5. A respirator cartridge according to claim 4 wherein said final filter components comprise an integral structure of resin bonded non-woven glass fibers.

6. A respirator cartridge according to claim 2 wherein said final filter is peripherally cemented to said shell.

7. A respirator cartridge according to claim 3 wherein said remaining prefilter components are compressingly fitted into said shell.

8. A respirator cartridge according to claim 7 wherein at least one of said prefilter components is further peripherally cemented to said shell.

* * * * *